(12) United States Patent
Wei et al.

(10) Patent No.: US 11,485,066 B2
(45) Date of Patent: Nov. 1, 2022

(54) PROCESSES FOR FORMATION OF POROUS BIOLOGICALLY COMPATIBLE SCAFFOLD STRUCTURES

(71) Applicant: Palo Alto Research Center Incorporated, Palo Alto, CA (US)

(72) Inventors: Junhua Wei, Mountain View, CA (US); Gabriel Iftime, Dublin, CA (US); Jessica Louis Baker Rivest, Palo Alto, CA (US); Anne Plochowietz, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 144 days.

(21) Appl. No.: 16/222,207

(22) Filed: Dec. 17, 2018

(65) Prior Publication Data

US 2020/0189177 A1   Jun. 18, 2020

(51) Int. Cl.
| | |
|---|---|
| *B05D 7/16* | (2006.01) |
| *B29C 64/10* | (2017.01) |
| *B82Y 5/00* | (2011.01) |
| *A61L 27/56* | (2006.01) |
| *B33Y 70/00* | (2020.01) |
| *B33Y 10/00* | (2015.01) |

(52) U.S. Cl.
CPC ............... *B29C 64/10* (2017.08); *A61L 27/56* (2013.01); *B05D 7/16* (2013.01); *B33Y 10/00* (2014.12); *B33Y 70/00* (2014.12); *B82Y 5/00* (2013.01)

(58) Field of Classification Search
CPC ....... B29C 64/10; B29C 64/106; A61L 27/56; A61L 27/44; A61L 2400/12; B33Y 80/00
See application file for complete search history.

(56) References Cited

U.S. PATENT DOCUMENTS

| | | | |
|---|---|---|---|
| 2009/0270519 A1* | 10/2009 | Cooper-White | ........... C08J 9/28 521/63 |
| 2017/0202811 A1* | 7/2017 | Wang | ..................... A61K 47/10 |
| 2018/0055643 A1 | 3/2018 | Castro et al. | |
| 2018/0085103 A1* | 3/2018 | Quintero | ............... A61L 24/046 |

OTHER PUBLICATIONS

Brey, "Vascularization: Regenerative Medicine and Tissue Engineering", CRC Press, Oct. 23, 2017, 397 pages.
Di Luca et al., "Gradients in pore size enhance the osteogenic differentiation of human mesenchymal stromal cells in three-dimensional scaffolds", Scientific Reports, 6, Article No. 22898, 2016, 13 pages.
Fan et al. "New approach for the treatment of osteoradionecrosis with pentoxifylline and tocopherol", Biomater Res. 18, 2014, 13 pages.

(Continued)

*Primary Examiner* — Hai Y Zhang
(74) *Attorney, Agent, or Firm* — Mueting Raasch Group

(57) ABSTRACT

A method of forming a porous structure involves mixing a solvent with a curable material which disperses in the solvent such that the mixture has greater than 50% solvent content. The mixture is deposited on a substrate and viscosity of the mixture is increased. The curable material in the mixture is cured while a shape of the curable material is maintained by the solvent. After curing, the solvent is removed from the structure.

25 Claims, 22 Drawing Sheets

(56) References Cited

OTHER PUBLICATIONS

Karageorgiou et al., "Porosity of 3D Biomaterial Scaffolds and Osteogenesis", Biomaterials 26 (27), Oct. 2005, pp. 5474-5491.
Nava et al., "The Effect of Scaffold Pore Size in Cartilage Tissue Engineering", J. appl Biomater Funct Mater, Jul. 26, 2016, pp. 223-229.
D'Brien et al., "The effect of pore size on cell adhesion in collagen-GAG scaffolds", Biomaterials 26(4), 2005, pp. 433-441.
D'Brien, "Biomaterials & Scaffolds for Tissue Engineering", Materials Today, vol. 14, Issue 3, Mar. 2011, pp. 88-95.
Woodfield et al., "Polymer scaffolds fabricated with pore-size gradients as a model for studying the zonal organization within tissue-engineered cartilage constructs", Tissue Eng Sep.-Oct. 2005, pp. 1297-1311.
Xiao et al., "The promotion of angiogenesis induced by three-dimensional porous beta-tricalcium pohospate scaffold with different interconnection sizes via activation of PO3K/Akt pathways", Scientific Reports 5: 9409, Mar. 2015, 11 pages.
Yannas et al., "Synthesis and characterization of a model extracellular matrix that induces partial regeneration of adult mammalian skin", Proc. Natl. Acad. Sci., vol. 86, Feb. 1989, pp. 933-937.

\* cited by examiner

PROCESSES FOR FORMATION OF POROUS BIOLOGICALLY COMPATIBLE SCAFFOLD STRUCTURES

BACKGROUND

Porous polymer structures are widely used in many industrial areas, such as packaging, insulation, impact protection, biomedical, membranes, and catalysts. Porous biologically compatible scaffolds play a crucial part in tissue engineering, and must meet key requirements such as excellent biocompatibility, large surface area for cell adhesion, high porosity, interconnected open pores for nutrient transport, and good mechanical properties for structural stability.

BRIEF SUMMARY

Some embodiments are directed to a method of forming a porous structure. A solvent is mixed with a curable material which disperses in the solvent to form a mixture comprising greater than 50% solvent content. The mixture is deposited on a substrate. The viscosity of the mixture is increased and the curable material in the mixture is cured while a shape of the curable material is maintained by the solvent. The solvent is removed from the structure.

According to some aspects, increasing the viscosity of the solvent comprises reducing the temperature of the mixture. The curable material is cured while the shape of the structure is maintained at the reduced temperature.

Some embodiments are directed to a method of forming a porous structure that involves simultaneously depositing a solvent and a mixture comprising a curable material which is dispersed in a solvent. The ratio of the solvent to the mixture comprising the curable material is controlled during the simultaneous deposition. The viscosity of the solvent in increased and the curable material is cured while a shape of the curable material is maintained by the solvent. After the curable material is cured, the solvent is removed from the structure.

The above summary is not intended to describe each embodiment or every implementation. A more complete understanding will become apparent and appreciated by referring to the following detailed description and claims in conjunction with the accompanying drawings.

BRIEF DESCRIPTION OF DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION OF ILLUSTRATIVE EMBODIMENTS

Three dimensional (3D) printed polymer composites can potentially replace heavy metal structures in industries where lightweighting is critical. The next development in lightweighting is represented by porous structures. However, the resolution of current printing technologies is limited by the nozzle size of the printers. Using current methods, porous polymer structures can be printed only by creating the pores with a 3D printing process. Because of the large nozzle size, e.g., for a fused deposition modeling (FDM) print process, only large pores (>100 micrometers) can be created, which result in weak structures. Thus, current printing technologies yield structures with low porosity and relatively thick pore walls which provide only limited improvement in weight saving.

Embodiments discussed herein provide methods for 3D printing porous polymer structures below the resolution of the 3D printing process such that the structures can have pore diameters that are smaller than the printer nozzle size. The disclosed approaches yield structures that have thin pore walls, high porosity (>50% porosity) and low shrinkage (<20% shrinkage). Embodiments described herein enable direct 3D printing of porous structures with increased toughness when compared to dense polymer composites and increase surface area of printed structures by increasing porosity. The ability to create 3D printed objects with pores that are much smaller than the voxel size enables creation of custom complex porous structures relevant to a new range of applications, particularly for structures with pore sizes in the submicron range.

For example, porous polymers possess a high specific toughness (toughness divided by weight), a high surface area, and are suitable for producing 3D printed structures that have lower density than polymer composites today. Additional applications include the potential to create biocompatible objects with well-defined porosity. The potential applications could include, but are not limited to, decreasing the weight of the core of a sandwich-structured composite, forming shape shock absorbers with graded porosity, directly printing electronic packaging, directly printing thermal/acoustic insulators, printing optimized structured catalyst carriers, printing hydrogen storage, printing structured gas/liquid filters, and printing tissue scaffolds.

Figure 1:
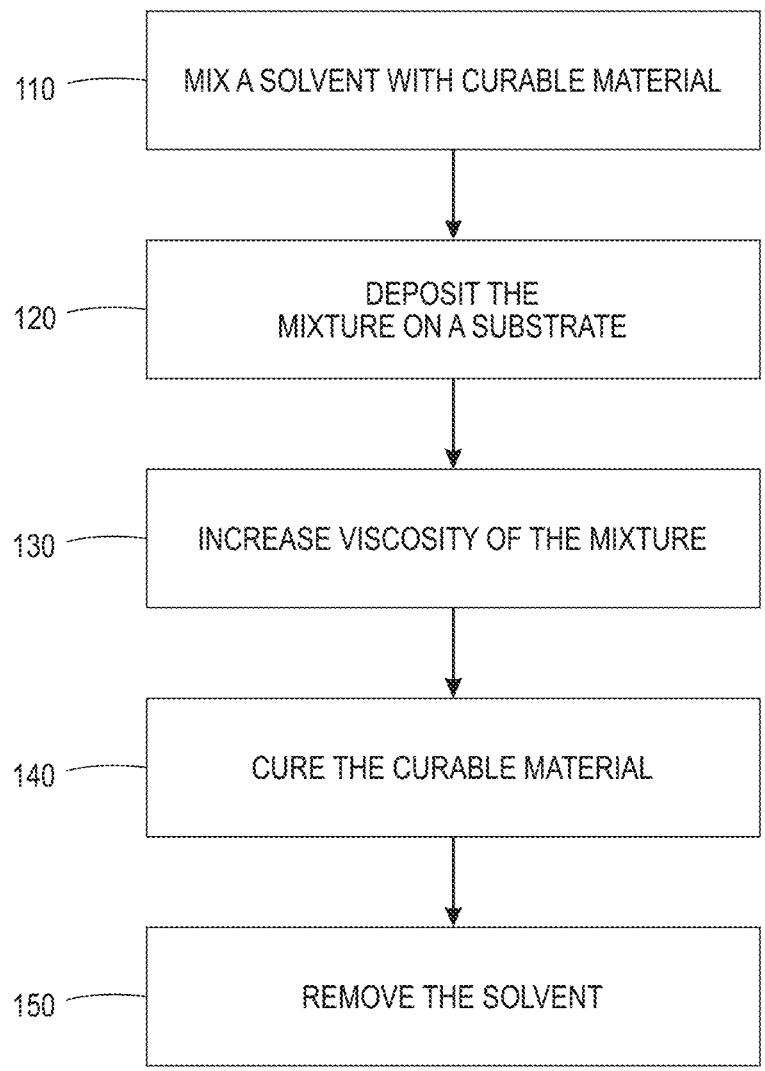
FIG. 1 is a flow diagram that illustrates a method for three dimensional (3D) printing porous polymer structures with a range of pore diameters including pore diameters that are below the resolution of the printing process in accordance with some embodiments.

FIG. 1 is a flow diagram of a method for 3D printing porous polymer structures with pore diameters that are below the resolution of the printing process, FIGS. 2A through 2D are conceptual drawings that illustrate the method outlined by the flow diagram of FIG. 1. The methods illustrated in FIGS. 1 and 2A through 2D can be used to fabricate biologically compatible porous polymer scaffolds.

Referring now to FIG. 1, the process involves mixing 110 a high melting temperature (Tm) solvent, e.g. a solvent having Tm>−20° C., with a curable material into a composite mixture. In some embodiments, the solvent comprises more than 50%, more than 60%, more than 70%, or more than 80% and/or less than 90% of the composite mixture. The solvent may comprise one or more of 1-octadecanol, water, diethylene glycol, triethylene glycol, tetraethylene glycol, decane, n-decanol, propylene glycol methyl ether acetate, ethyl-3-ethoxy propionate, 2-heptanone, and 2,3-dimethyl-4-heptanone. According to some implementations, the solvent comprises a crystalline molecule that melts at a temperature of about 10 degrees C. or more above the ambient temperature of the printing process.

The curable material may comprise monomers or polymers that are soluble in the solvent. In some embodiments, the curable material may be or comprise a thermoset material. In some embodiments, the curable material may be a thermoset material combined with a thermoplastic material. Suitable materials for the curable material include one or more of epoxy resin, polyester resin, polyurethanes, vulcanizable rubber, polyimides, silicone, and vinyl ester, for example. In embodiments in which a thermoplastic material is used, the thermoplastic material may comprise one or more of a polymer comprising lactide and glycolide, chitosan, hydroxybutyric acid, polyanhydrides, polyester, polyphosphazenes, polyphosphoester, caprolactone polymer, alginate, agar, polyurethane, and/or gelatin.

The composite mixture may additionally comprise fillers and/or nanoparticles. In some implementations, the composite mixture includes a curing initiator for the curable material. Alternatively or additionally, a curing initiator may be added after the composite mixture has been deposited and the solvent has solidified. In some embodiments, the filler may comprise a polymer.

The mixture is prepared above the Tm of the solvent so that a liquid solution is formed. The liquid solution is deposited 120 as a flowable ink. For example, the ink may be printed by extrusion or other printing methods such as ink jet. After deposition, the viscosity of the mixture is increased 130 such that the shape of the structure is maintained during curing. In some scenarios, increasing the viscosity of the mixture involves decreasing the temperature of the mixture to induce phase change. In another scenario, after or during deposition of the mixture, a chemical reaction and/or physical interaction is triggered that increases the viscosity of the mixture. For example, a chemical reaction that increases viscosity may involve a chemical reaction between the solvent molecules, a chemical reaction between the solvent molecules and additives in the mixture, and/or a chemical reaction between the additives in the mixture.

A physical interaction that increases the viscosity of the mixture may comprise an interaction between the solvent molecules themselves or between the solvent molecules and additives to the mixture. The solvent itself or an additive in the solvent may yield a non-Newtonian fluid which does not exhibit a constant viscosity independent of shear rate. A non-Newtonian fluid exhibits higher or lower viscosity at high shear rate, such as while flowing through a nozzle during the printing process. A non-Newtonian shear thinning material could be used to decrease the viscosity of the mixture while experiencing a high shear rate, e.g., during pushing through a print nozzle. After deposition, the shear rate is decreased and the viscosity of the mixture increases to maintain shape during curing. Alternatively, a non-Newtonian shear thickening material could be used in which the mixture becomes a gel at high shear rate during deposition and the mixture maintains its gelled shape for a period of time after deposition.

In some embodiments, viscosity control of the mixture may be achieved by adding soluble molecules that form hydrogen bonds or other types of non-chemical bonds when the mixture is at low shear, but release the bonds at high shear. In some embodiments, viscosity control of the mixture may be achieved by adding soluble molecules that form hydrogen bonds or other types of non-chemical bonds when the mixture is at high shear, but release the bonds at low shear. In some embodiments, the mixture may include particles that control the viscosity, such as two dimensional (2D) or one dimensional (1D) particles. The flow of the mixture can align the particle in a certain direction which induces shear thinning. In another example, the particles could interact with the solvent molecules or other additives to the mixture, such as by physically entangling or non-chemical crosslinking, to increase the viscosity at high flow rate which induces shear thickening.

Figure 2A:
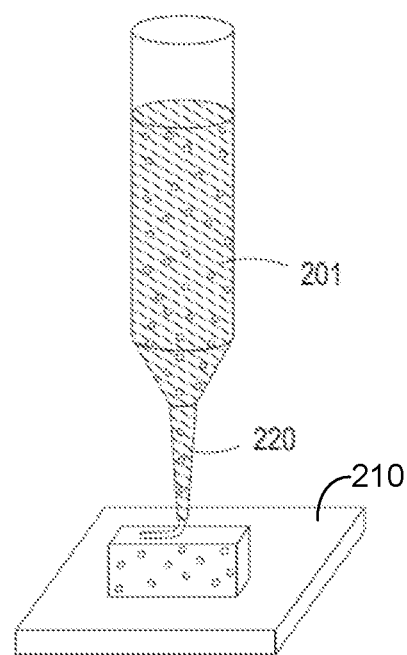
FIGS. 2A through 2D are conceptual drawings that illustrate the method of FIG. 1.

In some scenarios, the ink solidifies soon after it is ejected from the nozzle due to rapid cooling 130 below Tm in ambient conditions. FIG. 2A conceptually illustrates the mixture 201 being ejected from the nozzle 220 onto a substrate 210 and solidifying. Because of solidification, the 3D printed structure keeps its shape before the curable material is cured. Optionally, a curing initiator may be added to the structure after the solvent has solidified and before the curable material is cured. For example, the curing initiator may be introduced after solidification of the solvent by one or more of vapor diffusion and liquid permeation. In some embodiments, the curing initiator may be introduced after solidification of the solvent by active means of vapor deposition such as using sheath flow, air knife, and/or by applying negative pressure (vacuum suction).

Figure 2B:
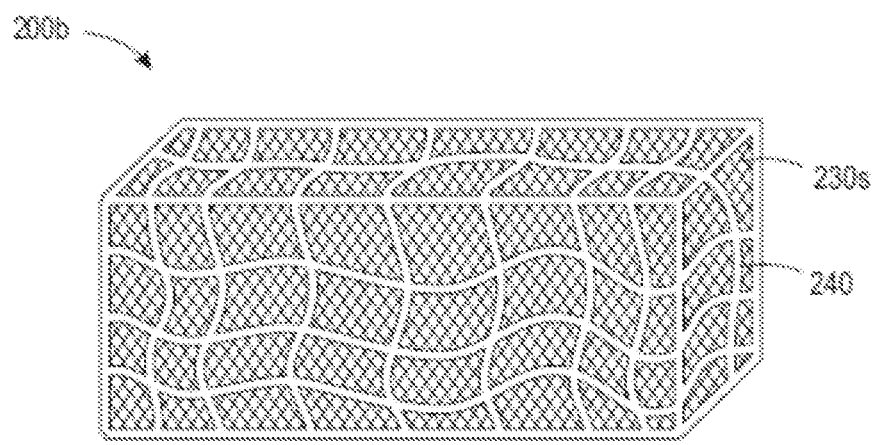

The curable material is cured 140 while the structure's shape is kept intact by the solidified solvent. For example, the curable material may self-cure, or curing may be activated, for example, by ultraviolet (UV) radiation, pressure, ultrasound, and/or other triggers. FIG. 2B conceptually illustrates a subassembly 200*b* comprising the solidified solvent 230*s* and cured material 240.

Figure 2C:
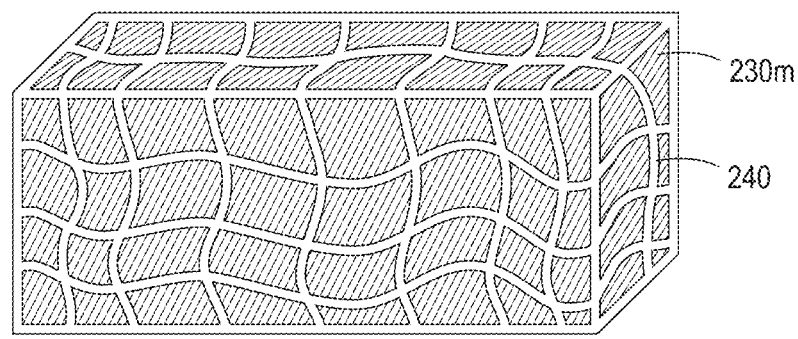
Figure 2D:
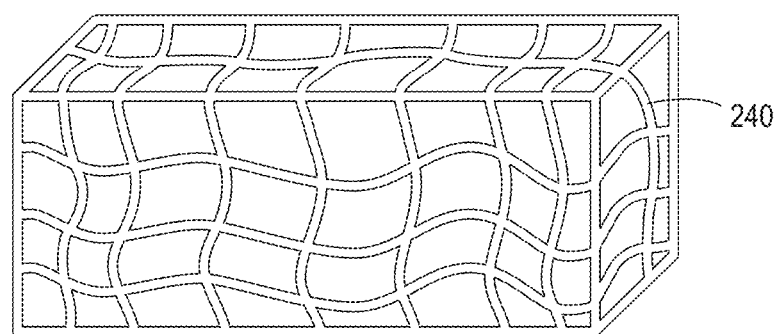

Once the curing step is complete, the solidified solvent is removed 150. The solvent can be removed, for example, by melting the solvent followed by vacuuming or by exchange with a second liquid solvent. For example, vacuum removal can involve applying the vacuum while the cured structure is kept at a high temperature that melts the solvent. Exchange with the second solvent may be accomplished using a second solvent that has a lower boiling temperature that the solvent used to form the structure. In some embodiments, the second solvent may be the solvent used to initially dissolve the solvent before the printing step. FIG. 2C illustrates the solvent 230*m* in the process of melting and removal. FIG. 2D shows the cured material 240 that remains after the solvent 230*m* is removed.

Figure 3:
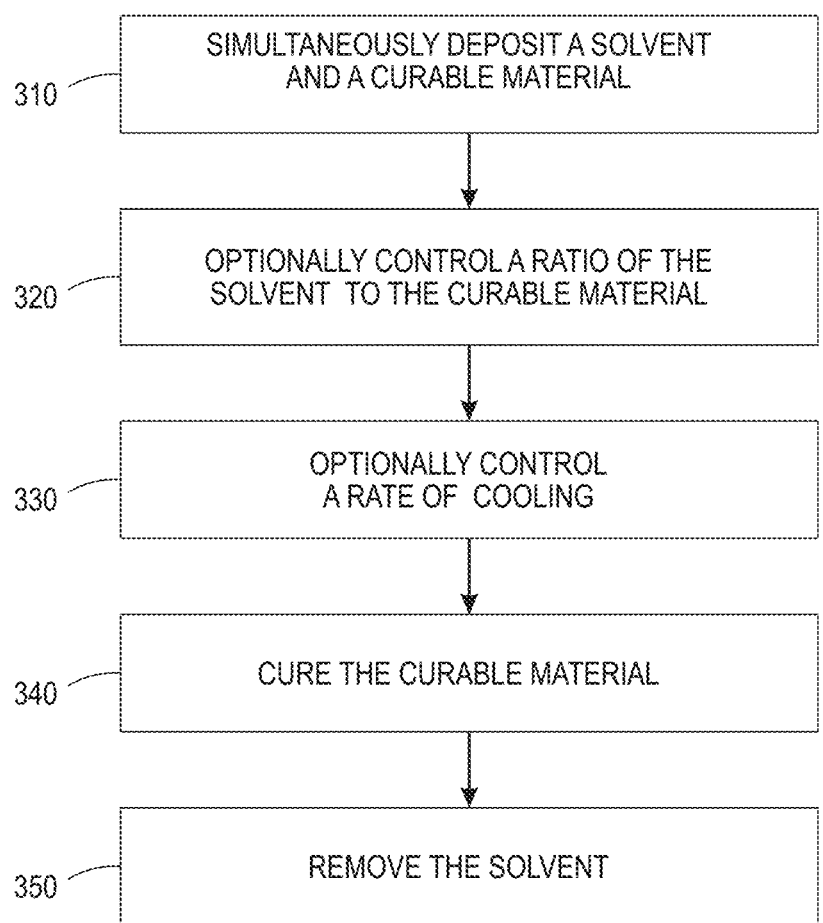
FIG. 3 is a flow diagram that illustrates a method for 3D printing porous polymer structures with a range of pore diameters including pore diameters that are below the resolution of the printing process in accordance with some embodiments.

FIG. 3 is a flow diagram of a method for 3D printing porous polymer structures with pore diameters that are below the resolution of the printing process. FIGS. 4A through 4D are diagrams that conceptually illustrate the method outlined in FIG. 3.

The process involves simultaneously depositing 310 a solvent and a curable material soluble in the solvent onto a substrate. The solvent may comprise any one or more of the solvent materials set forth herein. The curable material may comprise any one or more of the curable materials set forth herein. Additional materials such as curing initiators, nanoparticles, fillers, etc., can be added to the solvent and/or the curable material prior to deposition. For example, the solvent and the curable material may be simultaneously printed by co-extrusion or other printing methods such as ink jet.

Optionally the relative concentrations of solvent and curable material may be controlled 320 during the deposition process. In some implementations, the concentrations of solvent and the curable material can be controlled on-the-fly during deposition such that a concentration ratio of solvent to curable material changes as a function of deposition position along x,y, and/or z axes. For example, the concentrations of solvent and curable material may be controlled during deposition such that the solvent comprises more than 50%, more than 60%, more than 70%, or more than 80% and/or less than 90% of the composite mixture.

Controlling the solvent to curable material ratio controls the porosity of the final structure. Changing the ratio of solvent to curable material as a function of position during the deposition process can provide a porosity of the final structure that changes with distance along x, y, and/or z axes.

The solvent and curable material may mix during and/or after deposition. The solvent cools 330 after it is ejected from the nozzle. Optionally, the rate of cooling of the solvent can be controlled. The rate of cooling may be controlled to control pore size in the scaffold. Pores as referred to herein have at least two openings allowing fluid flow through the pores from the first opening to the second opening. The size of a pore is the diameter of the largest circle that can fit within the pore at all interior locations of the pore.

In some embodiments, the rate of cooling of the solvent can be controlled on-the-fly during deposition such that the rate of cooling changes as a function of deposition position along x,y, and/or z axes. Controlling the rate of cooling of the solvent controls the pore size in the final structure. Pores are not typically perfectly circular, for example, pores may be elliptical, or may have more complex shapes. The size of a pore can be characterized by the diameter of the pore. For example, controlling the rate of cooling may involve controlling the ambient temperature in the immediate vicinity of the freshly ejected material. For example, in some embodiments, the material may be ejected in a temperature controllable chamber or onto a temperature controllable substrate. Other methods of temperature control may include cooling via controlled influx of cold gases (e.g. liquid nitrogen cooling), and/or exchanging gases in the immediate vicinity of the ejected material.

The range of pore sizes in the scaffold may include pores having a larger pore size, e.g., greater than 100 μm pores having a smaller pore size, e.g., less than 50 μm, and pores having one or more intermediate pore sizes between the larger pore size and the smaller pore size. The entire range of pore sizes may extend along one, two, or three dimensions in the final structure.

Changing the ratio of solvent to curable material as a function of position during the deposition process can result in a final structure that has a range of pore sizes. For example, varying the solvent content as a function of position during deposition can provide a range of pore sizes, e.g., continuous and/or gradual variation of the solvent content during deposition.

Controlling the rate of increasing the viscosity as a function of position during the deposition process, e.g., by controlling the rate of cooling, can result in a final structure that has a range of pore sizes.

The range of pore sizes in the final structure can be obtained by varying the cure rate and/or degree of cure within the polymer precursors/solvent mixtures after deposition, followed by removal of unreacted (uncured) monomers. For example, a variable cure rate and/or degree of cure can be obtained using UV light of variable intensity in the case of UV curable monomers. As another example, a variable cure rate and/or degree of cure can be obtained for thermal curing for example with infrared (IR) beams of variable temperature in the case of epoxies or thermally initiated radical polymerization processes.

The range of pore sizes in the final structure can be obtained by incorporating a sacrificial additive, e.g., polystyrene particles, of variable size along one, two, or three dimensions within the material during deposition followed by removal of the additive by solvent extraction or by sublimation.

Figure 4A:
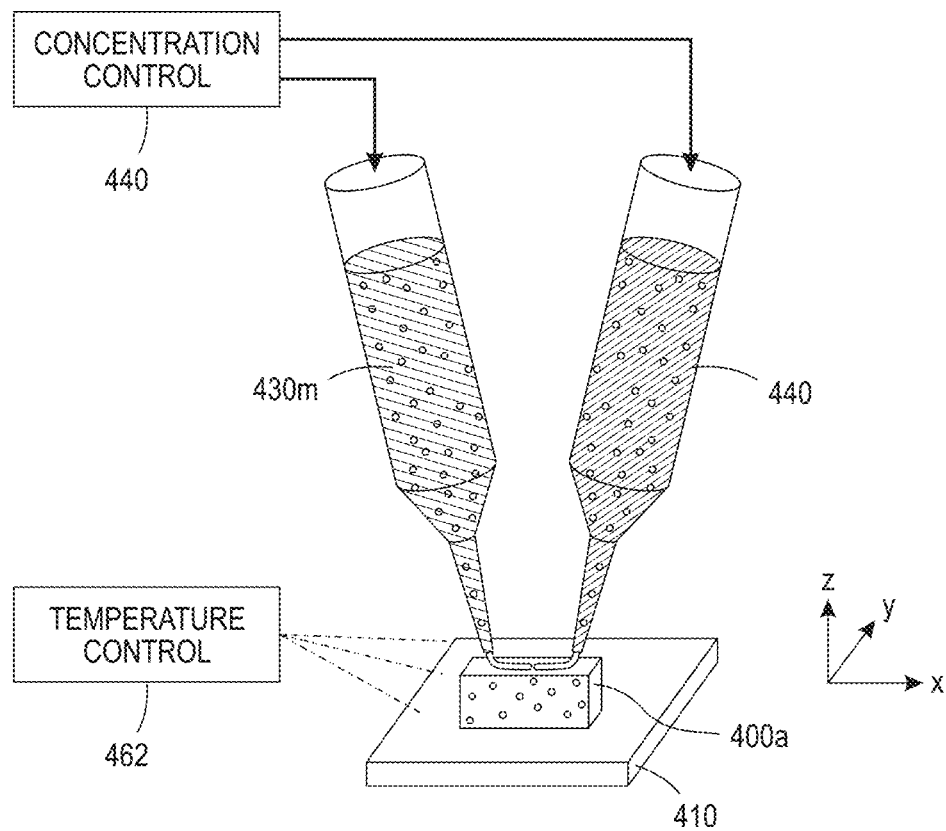
FIGS. 4A through 4D are conceptual drawings that illustrate the method of FIG. 3.

FIG. 4A conceptually illustrates simultaneous deposition, e.g., co-extrusion, of the solvent 430 and the curable material 440 onto a substrate 410. Because of solidification of the solvent 430, the 3D printed subassembly 400*a* shown in FIG. 4A keeps its shape before the curable material 440 is cured. Optionally, a controller 461 controls the relative concentrations of the solvent 430*m* and the curable material 440 in the composite mixture that is deposited. Optionally, a temperature controller 461 controls the temperatures of the mixture as it is cooling.

The curable material is cured 340 while the structure's shape is kept intact by the solid solvent. For example, the curable material may self-cure, or curing may be activated, for example, by ultraviolet (UV) radiation, pressure, ultrasound, microwave radiation and/or others triggers.

Figure 4B:
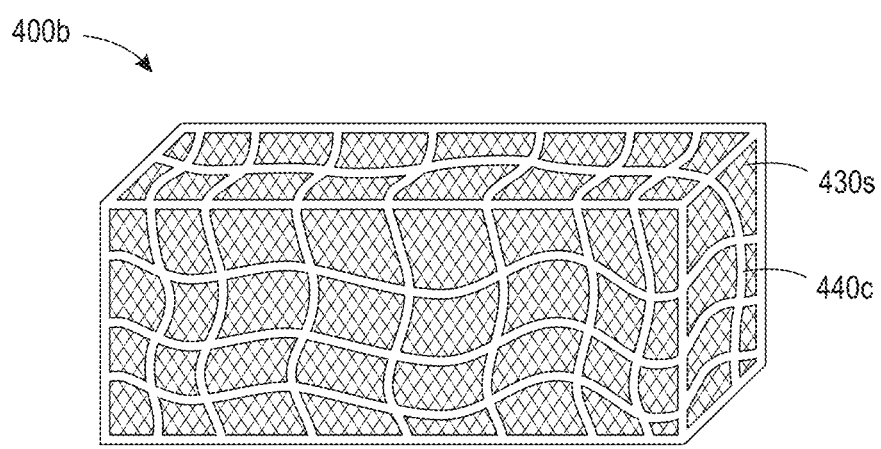
Figure 4C:
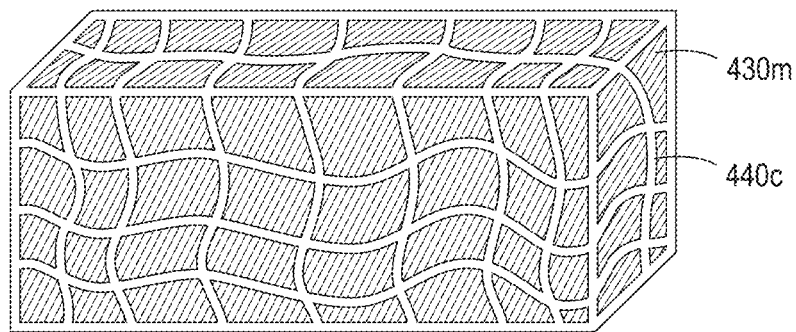
Figure 4D:
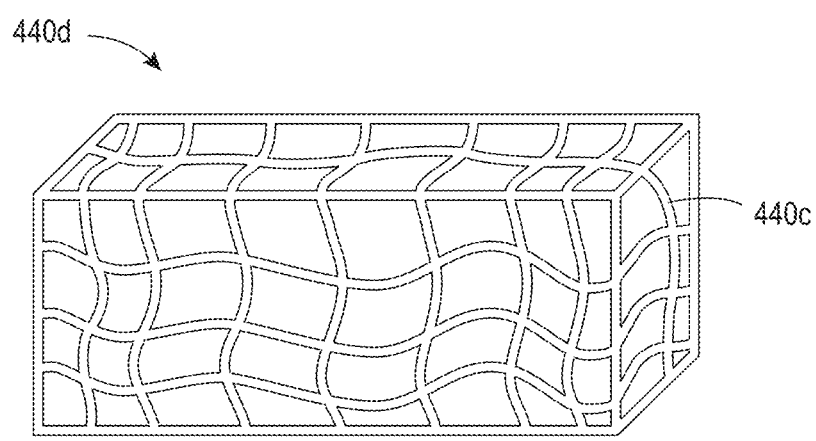

FIG. 4B conceptually illustrates a subassembly 400b comprising the solidified solvent 430s and cured material 440c. Once the curing step is complete, the solidified solvent is removed 350. The solvent can be removed, for example, by melting the solvent followed by vacuum or by exchange with a second liquid solvent. For example, vacuum removal can involve applying the vacuum while the cured structure is kept at a high temperature. Exchange with the second solvent may be accomplished when the second solvent has a lower boiling temperature than the solvent used to form the structure. In some embodiments, the second solvent may be the solvent used to initially dissolve the solvent before the printing step. FIG. 4C illustrates the solvent 230m in the process of melting and removal. FIG. 4D shows the final structure 400d comprising the cured material 440c that remains after the solvent 430m is removed.

The final structure 400d can include a range of pore sizes, including pores having a first larger pore size, a second smaller pore size, and one or more intermediate pore sizes between the larger pore size and the smaller pore size. At least some of the pore sizes are below a resolution of the deposition process used to form the structure 400d. The entire span of the range of pore sizes may extend along one, two, or three dimensions in the final structure. Changing the ratio of solvent to curable material as a function of position during the deposition process, controlling the rate of cooling as a function of position during the deposition process, varying the cure rate and/or degree of cure within the polymer precursors/solvent mixtures after deposition, and/or incorporating a sacrificial additive along one, two, or three dimensions within the material during deposition followed by removal of the additive can provide a porosity of the final structure that changes with distance along x, y, or z axes. The pores can occupy more than 50%, more than 60%, more than 70% more than 80% and less than 90% of the volume of the structure 400d. Changing the cooling rate as a function of position during the deposition process can provide pores having pore sizes that change as a function of distance along x, y, or z axes. The range of the pore sizes can include pores that are less than the resolution of the deposition process, e.g., less than 50 µm, and pores that are greater than the resolution of the deposition process, e.g., greater than 100 µm, along with pores of one or more intermediate sizes.

The disclosed 3D printing processes are particularly useful to fabricate biologically compatible 3D porous scaffold structures useful for tissue engineering. Scaffolds must meet key requirements such as excellent biocompatibility, large surface area for cell adhesion, high porosity, interconnected open pores for nutrient transport, and good mechanical properties for structural stability.

The printing processes discussed herein enable 3D printing of porous biocompatible scaffolds with pore sizes ranging down to tenth of micrometer and up to a millimeter or even a centimeter, spanning multiple biologically relevant length-scales. The printing processes allow scaffolds to be formed having pores with at least two separate openings (which are referred to herein as "open pores" or simple "pores") that are fluidically connected and having a wide range of different sizes. Additionally the scaffold may include compartments and/or pits having only one opening. The scaffold may include pores having a range of sizes wherein pore sizes that span the entire range of pore sizes extend along one, two, or three dimensions. The range can include pores having a pore size of less than 100 µm, less than 75 µm, or less than 50 µm, pores having a pore size greater than 100 µm, greater than 150 µm, greater than 200 µm, or greater than several millimeters. The larger pores can act as channels through the scaffold. One or both of pore size and porosity of the scaffold may vary as a function of distance in one, two, or three dimensions.

Pore pitch is the center-to-center distance between two neighboring pores and is a function of the size of the pores. The center of a pore can be defined by the center of mass of the pore volume V. The pore volume again can be defined as the volume of fluid V that is held between/within all (at least two) openings of the pore. Relative pore pitch is the ratio of the center-to-center distance between pores (pore pitch) divided by the average diameter of the neighboring pores along the pitch axis. According to some embodiments the scaffold may have a gradient of relative pore pitches that extends along one, two, or three orthogonal axes within the scaffold. In some embodiments, the range of relative pore pitches ranges from slightly larger than the average diameter of the neighboring pores along the pitch axis to about twice the average diameter of the neighboring pores along the pitch axis. This range in relative pore pitch reflects porosity values of about 90% to about 50%.

Porosity and pore size regimes that can be achieved by the 3D printed scaffolds disclosed herein are comparable to microvasculature structures, thus different biological tissues such as skin, liver, kidney, etc. can be mimicked. This printability enables scaffold structures with tunable pore sizes ranging from 10 µm to several millimeters or even centimeter as well as tunable porosity of 50% to 90%. At porosities >50%, the structures fabricated using the disclosed approaches exhibit superior mechanical modulus of >20 MPa and/or compressive strength of about 1 MPa. In addition, the printing processes described herein can be used to fabricate structures having 60 degree to 130 degree overhangs with porosity greater than 50%. The contact angle of the biologically compatible material is sufficient to support nutrient flow through the scaffold. For example, the biologically compatible material may have a contact angle in a range of about 0 degrees to about 65 degrees.

The scaffold structure includes a biologically compatible material, which is deposited as a curable material and is then cured. The biologically compatible material may comprise one or more of a radiation curable material, a thermally curable material, and a self-curable material, for example. Suitable biologically compatible curable materials for forming the scaffold can include oligomer of biocompatible/biodegradable polymer, biocompatible/biodegradable polymer with curable terminate/sites; monomer of biocompatible/biodegradable polymer. The biocompatible polymer may include natural polymer, e.g. proteins, rubbers, alginate, agar, etc., synthetic polymers e.g. polyethylene glycol etc., and/or semi synthetic polymers, e.g. rayon etc. The biodegradable polymer can include: synthesized polymer, such as polylactides, poly(lactide-co-glycolide), polyglycolide, polydioxanone, polyesters, polyphosphazenes, polyphosphoesters, chitosan, caprolactone polymers etc. The biologically compatible material may comprise a thermoset material, an organic or an inorganic material, a carbon based material, ceramic, polymer, clay, poly(methyl methacrylate) (PMMA), graphene, bone cement, epoxy, polyester resin, polyurethane, vulcanizable rubber, polyimides, silicone, vinyl ester. The biologically compatible material may be a composite material that includes any one or more of the materials set forth above along with additional materials.

Figure 5A:
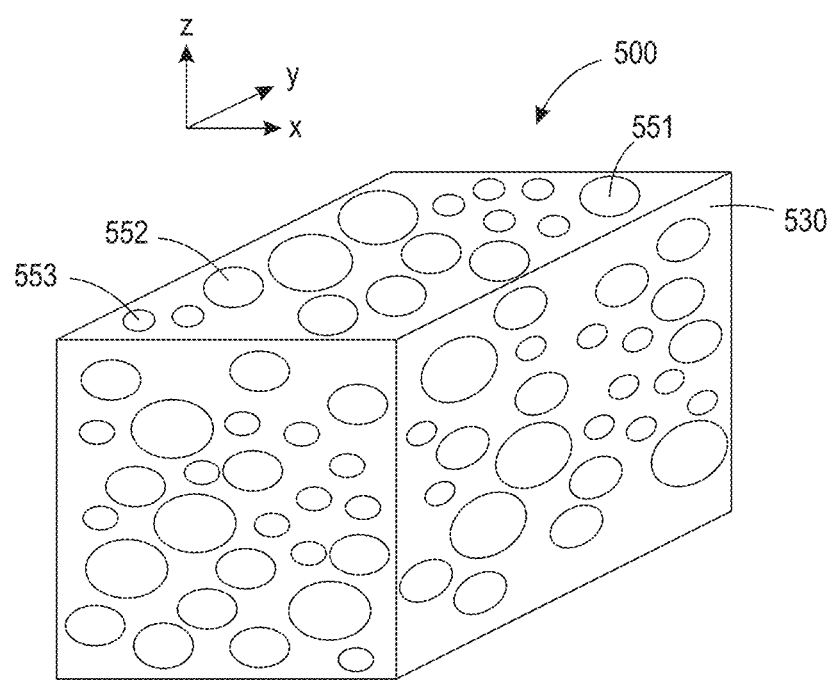
FIG. 5A provides an idealized perspective drawing of a portion of a three dimensional biological scaffold structure which is used to illustrate certain features of the scaffold structure in accordance with some embodiments.
Figure 5B:
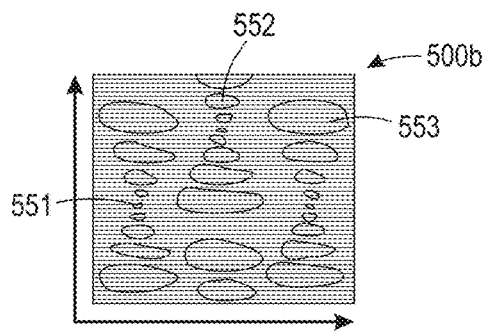
FIGS. 5B-5H are diagrams of idealized two dimensional cross sections representing possible scaffold configurations in accordance with various embodiments.
Figure 5C:
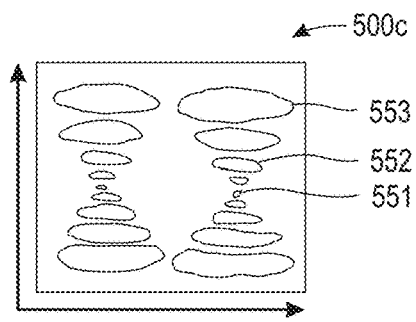
Figure 5D:
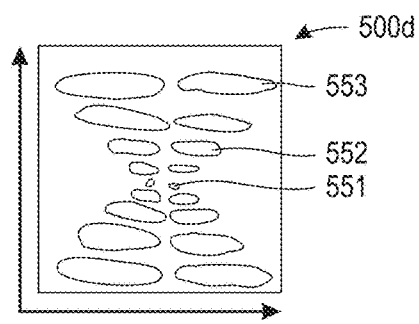
Figure 5E:
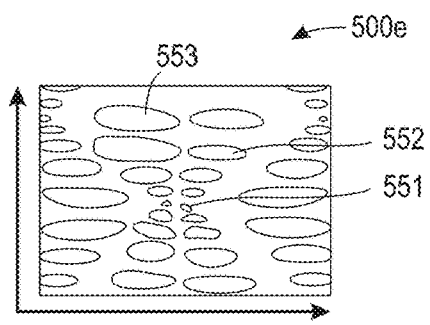
Figure 5F:
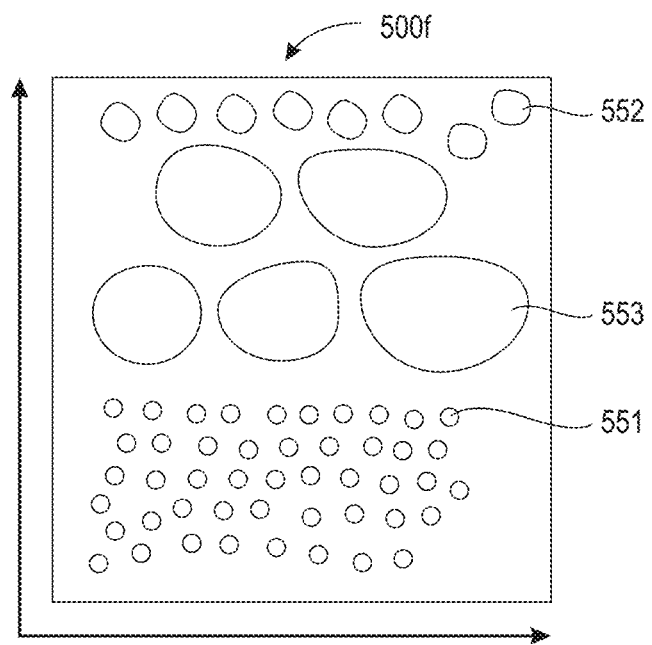
Figure 5G:
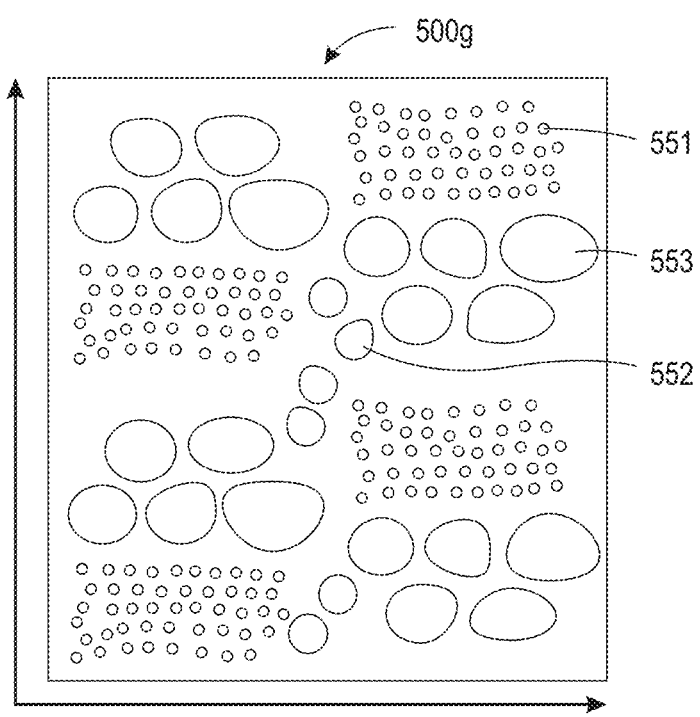
Figure 5H:
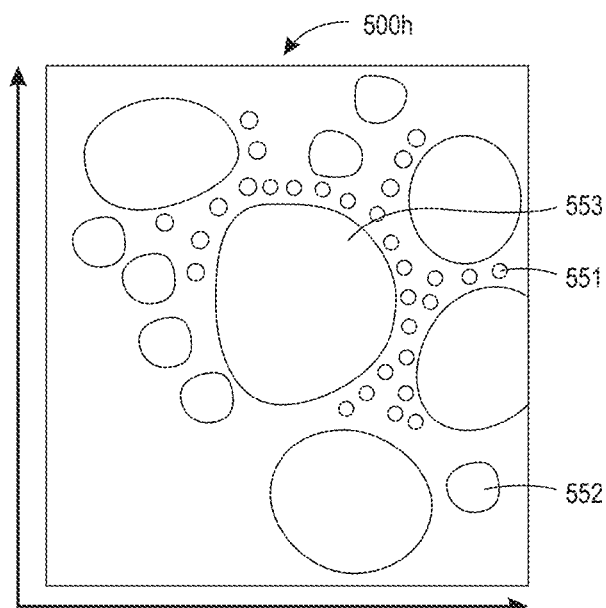

FIG. 5A provides an idealized perspective drawing of a portion of a three dimensional biological scaffold structure 500 which is presented to illustrate certain features of the scaffold structure. The biologically compatible material 530 forms the walls of multiple pores 551, 552, 553 in a range of different sizes, The range can include one or more pores 551 having a pore size of less than 100 µm, less than 75 µm, or less than 50 µm, or less than 20 µm, and one or more pores 553 having a pore size of greater than 100 µm, greater than 150 µm, or greater than 200 µm, and can also include one or more pores 552 having one or more intermediate pore sizes between the size of the smaller pores 551 and the size of the larger pores 553. The pores 551, 552, 553 may have regular or irregular shapes. The size of the pores as well as the porosity of the structure 500 may vary with distance along any of the x, y, and/or z axis. The scaffold may comprise pores having a range of pore sizes such the pores disposed along each of one, two or three orthogonal axes span the entire range of pore sizes.

The pores allow fluid to flow into the pore at a first opening of the pore and to flow out of the pore through a second opening, different from the first opening. A pore can have branches leading to three or more openings. Some of the pores may have openings at the surface of the scaffold, with the pore extending into the interior of the scaffold. Many of the pores 551, 552, 553 may be interconnected. As previously discussed, the pores 551, 552, 553 occupy more than 50%, more than 60%, more than 70%, or more than 80% and/or less than 90% of a volume of the scaffold structure 500. The porosity of the scaffold structure can be greater than 50%, greater than 60%, greater than 70%, or greater than 80% and/or less than 90%. The surface area of the structure 500 can be greater than or equal to about 8 m$^2$/g.

FIGS. 5B-5H illustrate diagrams of two dimensional cross sections 500b-500h representing possible idealized scaffold configurations. The cross sections 500b-500h are shown in reference to horizontal and vertical axes and can represent cross sections of the scaffold 500 taken in any of the x-z, x-y, or y-z planes.

Each of the scaffold cross sections 500b-500h includes pores in a range of pore sizes including one or more larger sized pores, 553 one or more smaller sized pores 551, and one or more pores 552 having sizes between the larger sized pores and the smaller sized pores. The pores in each cross section 500b-500h span the range of pore sizes along one or both of the horizontal and vertical axes.

Figure 6:
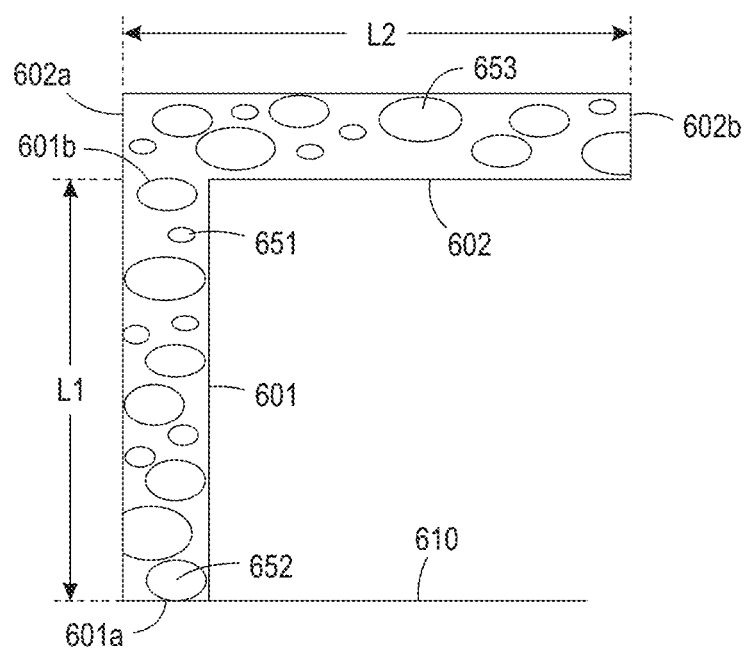
FIG. 6 is a diagram of an overhang region that may be included in a 3D porous structure fabricated in accordance with some embodiments.
Figure 7:
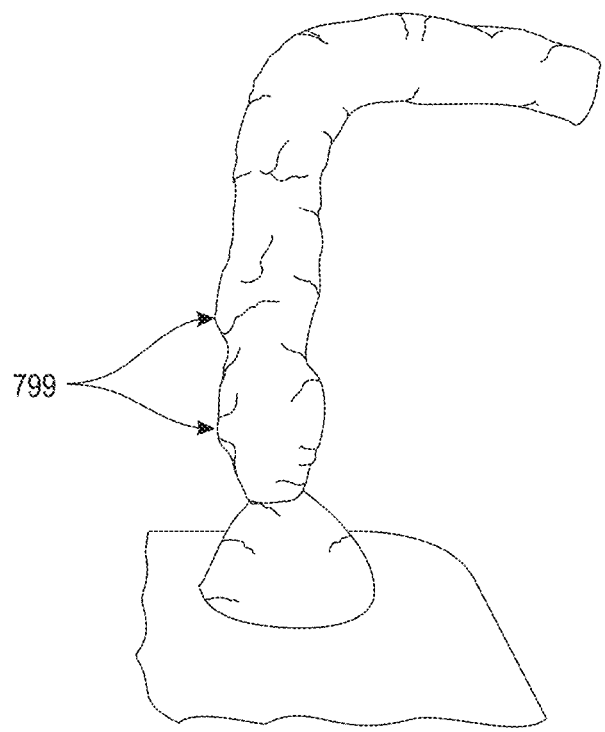
FIG. 7 is a photograph of a freestanding overhang region in accordance with some embodiments.

In some embodiments, a 3D structure may include at least one freestanding overhang region 600, conceptually illustrated in FIG. 6. The freestanding overhang region 600 includes an elongated first portion 601 comprising a material 630 that forms walls of multiple pores 651, 652, 653 that occupy more than 50% of a volume of the first portion 601, In various implementations, the first portion 601 may have a porosity of more than 50%, more than 60%, more than 70% more than 80% and less than 90%. The first portion 601 has a first end 601a and a second end 601b. The first end 601a is attached to a base 610 and the first portion 601 extends away from the base 610. The region 600 includes an elongated second portion 602 comprising a material that forms walls of multiple pores 651, 652, 653 that occupy more than 50% of a volume of the second portion 602. In various implementations, the second portion 602 may have a porosity of more than 50%, more than 60%, more than 70% more than 80% and less than 90%. The second portion 602 has a first end 602a and a second end 602b that is free. The first end 602a of the second portion 602 is attached to the second end 601b of the first portion 601. The second portion 602 overhangs the base 610 and may be oriented at an angle between about 60 degrees and about 120 degrees with respect to the first portion 601. The first portion has a length L1 and the second portion has a length L2, wherein a ratio of L2/L1 may be greater than or equal to 0.5, greater than or equal to 0.75, greater than or equal to 1, or greater than or equal to 1.25. FIG. 7 is a photograph of a freestanding overhang region as described with reference to FIG. 6. Artifacts, e.g., slight scalloped areas 799 indicative of the printing process can be seen.

According to some embodiments, solvents or mixture of solvents such as water, 1-octadecanol, diethylene glycol, triethylene glycol, tetraethylene glycol, decane, n-decanol, propylene glycol methyl ether acetate, ethyl-3-ethoxy propionate, 2-heptanone, 2,3-dimethyl-4-heptanone, etc. can be added to mixtures of thermoset and/or thermoplastic monomers such as epoxy resin, polyester resin, polyurethanes, vulcanizable rubber, polyimides, silicone, vinyl ester, and lactide and glycolide, chitosan, hydroxybutyric acid, polyanhydrides, polyester, polyphosphazenes, polyphosphoester, caprolactone polymer, alginate, agar, polyurethane, gelatin. The solvent-monomer components are mixed at temperatures at which the solvent is liquid, for example temperatures T>10° C. The solvent-monomer mixture is printed in a temperature-controlled way at temperature ranges close to the curing temperatures of the respective monomers. For example, the solvent-monomer mixture may be printed onto a temperature-controlled substrate and/or in a temperature-controlled chamber. The printed subassembly may be kept temperature stabilized for several days. The solvent is removed from the subassembly after the monomer components are cured. For example, the subassembly can be heated above the melting temperature of the respective solvent after which the solvent may be vacuum extracted.

Figure 8:
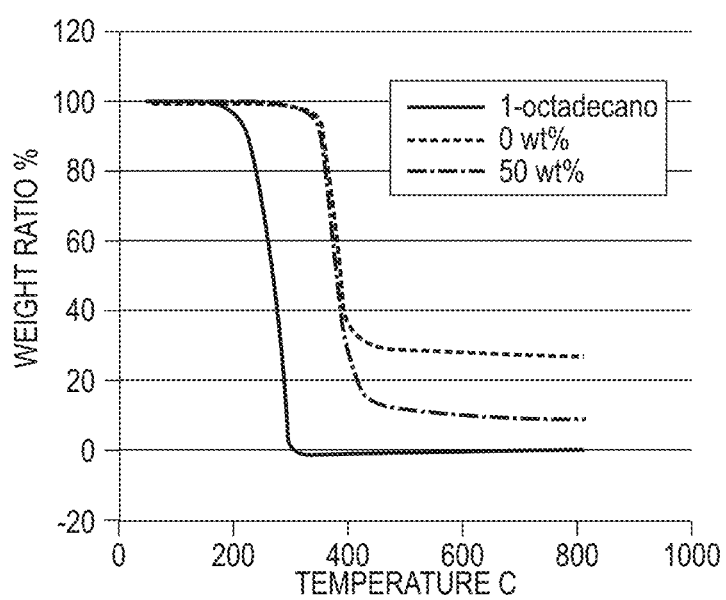
FIG. 8 provides graphs of thermogravimetric analysis for pure solvent, 0 wt % solvent and 50 wt %, solvent.

The leftover of a solvent after the printing procedure outlined above was examined by thermogravimetric analysis (TGA) for concentrations of solvent: 0 wt %, 50 wt %, 75 wt %, and 90 wt %. As illustrated in the graphs of FIG. 8, mass loss was observed with pure solvent. The 50 wt % porous polymer material shows no mass loss, which indicates the complete removal of the solvent.

In order to determine the porosity of the printed samples, the density and the surface area were measured. The density can be used to calculate the porosity according to equation:

$$\% \text{ Porosity} = \left(1 - \frac{\text{bulk density}}{0 \text{ wt \% density}}\right) \times 100, \qquad [1]$$

wherein the bulk density is the density of bulk samples; and the 0 wt % density is the density of the pure cured polymer.

The theoretical porosities and densities of samples were calculated from the theoretical densities and wt % of each of the composites in the samples. The measured densities were calculated by dividing the weight (measured by balance) by the volume (measured by water displacement). The shrinkage was calculated by dividing measured porosity. The shrinkage was calculated using the equation:

$$\% \text{ Shrinkage} = \left(1 - \frac{\text{theoretical density}}{\text{measured density}}\right) \times 100.$$

In order to determine the surface area of the samples, Brunauer-Emmett-Teller adsorption method is used. The morphologies of the porous material were investigated by SEM.

Table 1 summarizes the results of densities and calculated porosities of some prepared samples.

Porosity of the printed samples were confirmed, and porosities as high as ~65% have been achieved. The porosity is further confirmed by the Brunauer-Emmett-Teller (BET) analysis results which indicate that the 50 wt % sample doubled the surface area of pure cured polymer due to the porous structure.

TABLE 1

| wt % of solvent | 0% | 50% | 75% |
|---|---|---|---|
| Theoretical density (g/cc) | 1.16 | 0.48 | 0.22 |
| Theoretical porosity (%) | 0 | 58.8 | 81.1 |
| Measured density (g/cc) | 1.16 | 0.58 | 0.41 |
| Measured porosity (%) | 0 | 50.0 | 64.7 |
| Shrinkage (%) | 0 | 17.2 | 46.3 |
| BET (m²/g) | 4.07 | 8.65 | 8.24 |

Figure 9:
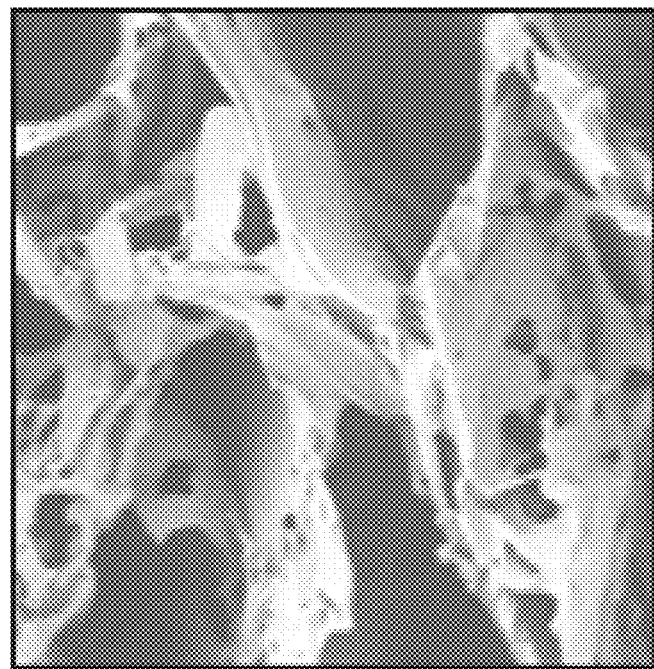
FIG. 9 is a scanning electron micrograph (SEM) of sample at 50 wt % solvent in accordance with some embodiments.
Figure 10:
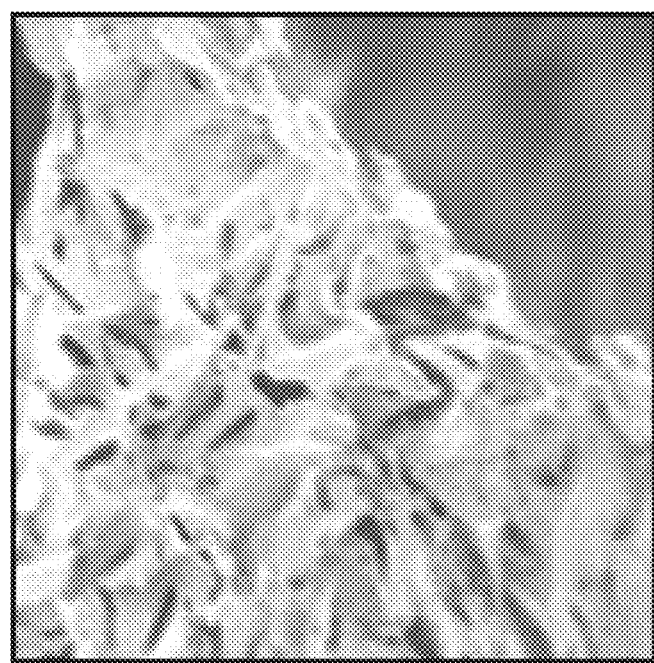
FIG. 10 is a SEM of sample at 75 wt % solvent in accordance with some embodiments.
Figure 11:
FIG. 11 is a SEM of sample at 90 wt % solvent in accordance with some embodiments.

While the density measurements indicate porosities of up to 65%, the BET surface areas are quite small by the standards of polymer aerogels. Further characterization was obtained by SEM analysis shown in FIG. 9 (50 wt %), FIG. 10 (75 wt %), and FIG. 11 (90 wt %). It can be seen that a porous structure made with 50% solid solvent contains very large pores of the order of 10s of microns.

Shrinkage is one of the key factors for 3D printing especially for graded structure printing. Due to the porous structure and capillary force during extracting solvent, 10-40% of shrinkage is expected for most porous polymer preparations without reinforcement. In this example, shrinkage increases according to the increasing of wt % of solvent due to the weaker support of the porous polymer during solvent extraction. The SEM images confirmed that higher solvent % results in increased shrinkage and smaller pores.

Figure 12:
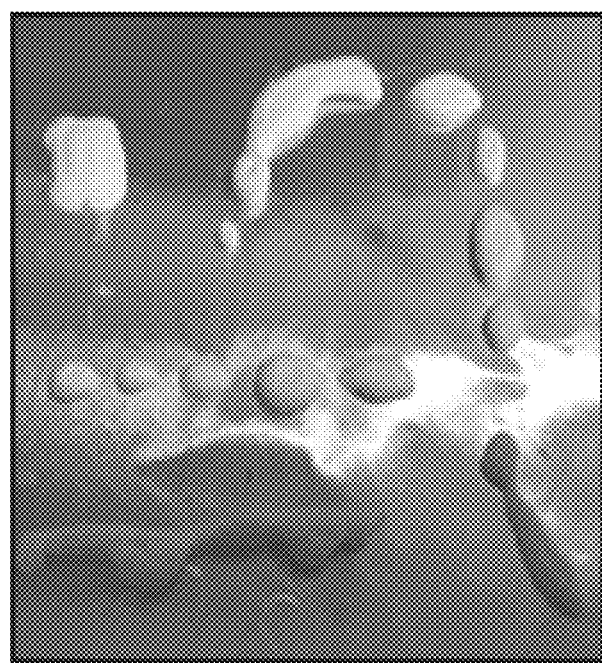
FIG. 12 is a photograph of a sample prepared by drop deposition with 50 wt % solvent in accordance with some embodiments.
Figure 13:
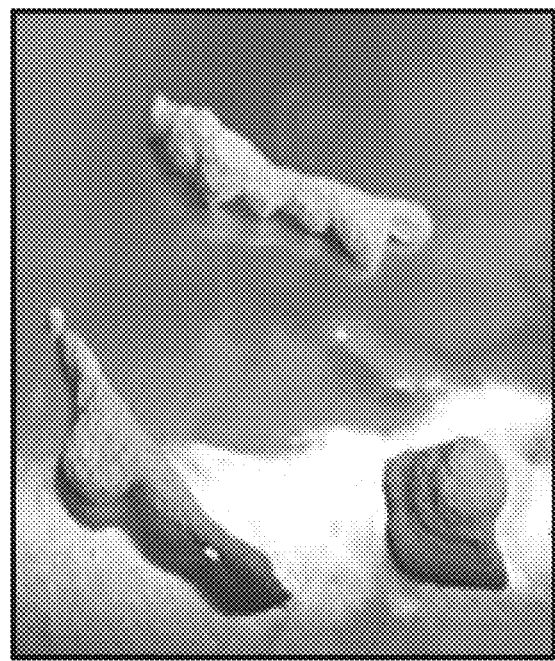
FIG. 13 is a photograph of a sample prepared by drop deposition with 75 wt % solvent in accordance with some embodiments.
Figure 14:
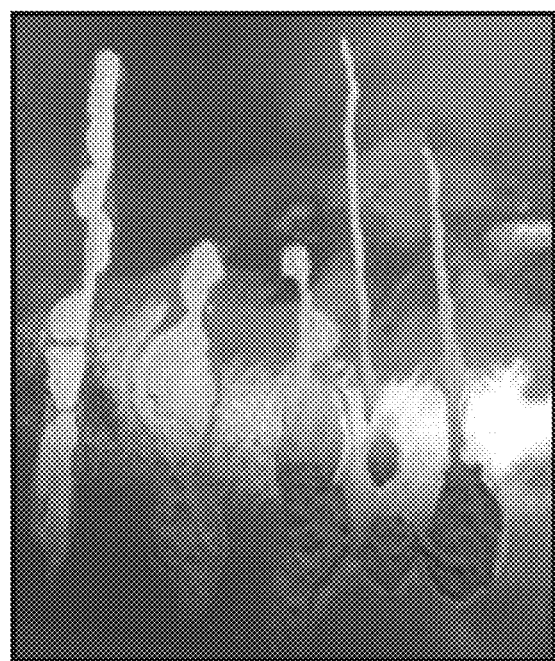
FIG. 14 is a photograph of a sample prepared by drop deposition with 90 wt % solvent in accordance with some embodiments.

The pictures of the 3D printed 50 wt %, 75 wt %, and 90 wt % samples prepared by using drop deposition are presented in FIG. 12 (50 wt % solvent), FIG. 13 (75 wt % solvent), and FIG. 14 (90 wt % solvent). The 50 wt % sample shows round drop shape and clear layer structure which indicate good shape fidelity. Due to the shrinkage, the surface of 75 wt % sample is no longer smooth as with the 50 wt % sample. But still the shape of the drop can be figured out as well as the layer. The 90 wt % sample collapsed and the printed structure can no longer be discerned.

This comparison indicates that the shape can still be well preserved at 50 wt % solvent. However, collapse begins to influence the shape at 75 wt %. Above 75 wt %, shape fidelity is significantly degraded.

The maximum size of a printed bulk could be infinity due to the fast extrusion rate by using a syringe pump. However, it may take some time to evaporate solvent from the cured bulk because the melted solvent is evaporated into the air and diffused out. To verify how large a bulk could be printed, a model based on the solvent evaporation process and diffusion was calculated.

Figure 15A:
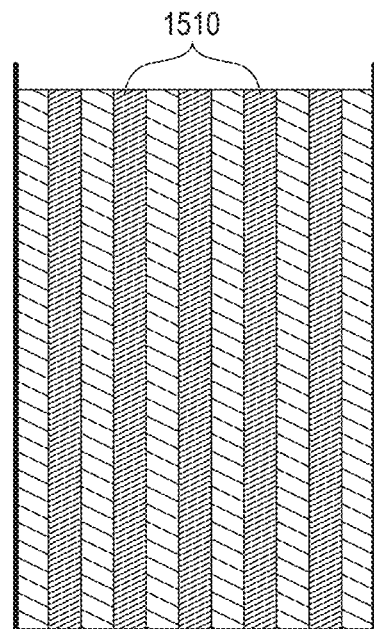
FIGS. 15A and 15B are diagrams illustrating a simplified model of a porous structure comprising an array of polymer channels filled with solvent that is useful for estimating evaporation rate of the solvent from a porous structure.

The evaporation of the solvent in the cured porous polymer can be simplified to a model comprising an array of polymer channels 1510 filled with the solvent as depicted in FIG. 15A. The evaporation of the melted solvent starts at the liquid-air surface and forms a vapor pressure at certain temperature. The diffusion of the vapor layer to the air above it generates the evaporation rate. In order to calculate the evaporation rate, vapor pressure at evaporation condition, the diffusion rate needs to be estimated.

The vapor pressure at 125 degrees C. (evaporation temperature) is calculated by Clausius-Clapeyron equation:

$$\ln\left(\frac{P1}{P2}\right) = \frac{\Delta H_{vap}}{R}\left(\frac{1}{T2} - \frac{1}{T1}\right)$$

where the P is vapor pressure (Pa) and T is temperature (K). From the NIST library, the calculated vapor pressure for a common solvent used here at 125 C is ~200 Pascal.

The evaporation rate of the solvent is estimated as the product of the saturated vapor concentration and a mass-transfer coefficient. The velocity of the saturated air layer been removed can be calculated by:

$$ER = PMk(RT)^{-1}$$

where R is gas constant, $k = DY^{-1}$, D is diffusion coefficient and Y is diffusion path length, M is molecular weight. There are two variables need to be determined D and Y. The diffusion coefficient can be calculated by the Chapman-Enskog Model:

$$D^{eff} = \frac{\phi}{\tau}D$$

$$D = \frac{0.00186 T^{\frac{3}{2}}}{P\sigma^2 \Omega}\left(\frac{1}{Mi} + \frac{1}{Mj}\right)^{1/2}$$

For a common solvent, the D is calculated to be ~0.0005 mm²/hr.

Figure 15B:
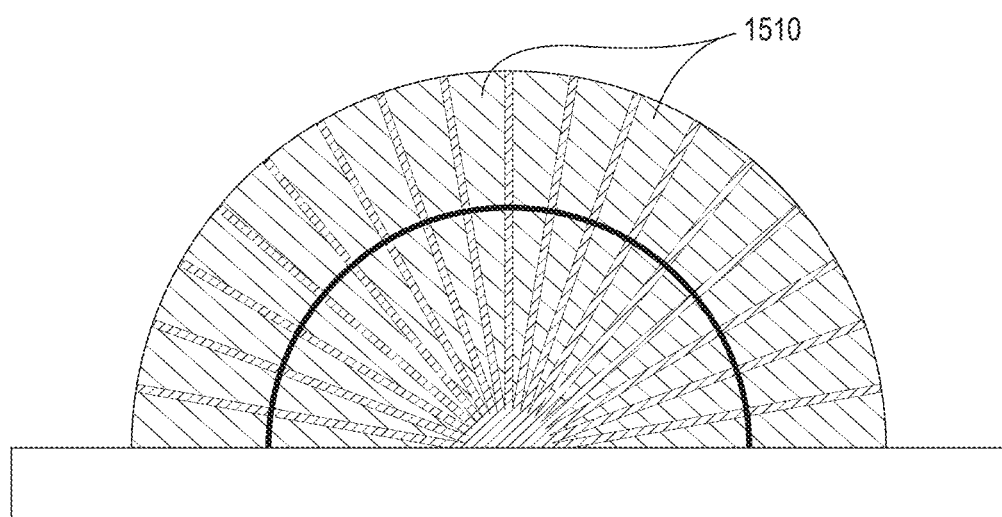

Y is the diffusion path length which is not a constant value in the channel model. To better estimate evaporation, a half sphere model was established as seen in FIG. 15B. In this model, the solvent is evaporated from the outer surface to the inner part. Due to the depth of the interface layer, the diffusion path length Y changes. Assuming there is 1 g of printed half sphere with 50 wt % of a common solvent in it:

$$D^{eff} = \frac{\phi}{\tau}D = 0.0005 * 0.588 = 0.00025 \text{ mm}^2/\text{hr},$$

$$k = D^{eff} Y^{-1} = 0.00025/(0.794 - r) \text{ mm/hr},$$

$$ER = 637.15 * k = 0.16/(0.794 - r)\left(\frac{g}{\text{mm}^2 * \text{hr}}\right)$$

$$t = \int \frac{\text{solvent mass}}{\text{solvent surface} * ER}$$

$$dr = \int \frac{2\pi r^2 * 0.5}{2\pi r^2 * Sr * ER}$$

$$dr = \int_0^{0.794} \frac{(0.794 - r) * 0.5}{Sr * 0.24} \approx 1 \text{ hr}$$

Thus, the model predicts it will take about 1 hr to evaporate a 1 g 50 wt % cured bulk at evaporation condition.

Figure 16:
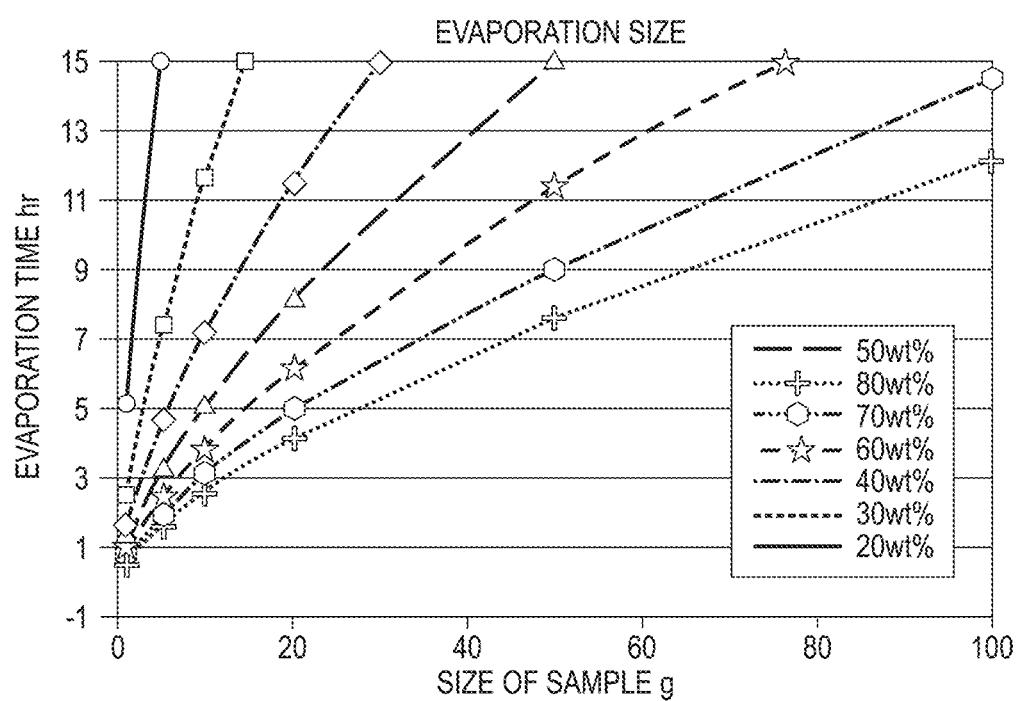
FIG. 16 provides a family of graphs that illustrate the evaporation time vs. the weight of the sample for samples having different solvent concentrations.

The maximum reasonable time to evaporate a sample is overnight, e.g., about 15 hr. For different solvent concentration, the weights of the printed bulk under reasonable time are quite different. FIG. 16 provides a family of graphs that illustrate the evaporation time vs. the weight of the sample for samples having different solvent concentrations. It will be appreciated from FIG. 16 that the higher the concentration of solvent, the larger the weight of the sample that can be evaporated within the overnight time frame. For a cured bulk made with >50 wt % solvent ink, a 50 g or 2.8 cm diameter half sphere sample can be prepared overnight.

The bulk shape also significantly influences the size that can be evaporated in time. Table 2 provides the estimated volume and side length for some shaped samples evaporated overnight. Due to the smallest surface area vs. volume, the printed bulk in the half sphere is the smallest of all kind of shapes.

TABLE 2

| Shape | tetra-hedron | cube | dodeca-hedron | Half sphere | Half capsule |
|---|---|---|---|---|---|
| Volume cm³ | 75 | 62 | 55 | 50 | 54 |
| Side length cm | 8.5 | 4.0 | 1.9 | 2.2 | 3.7 |

Figure 17A:
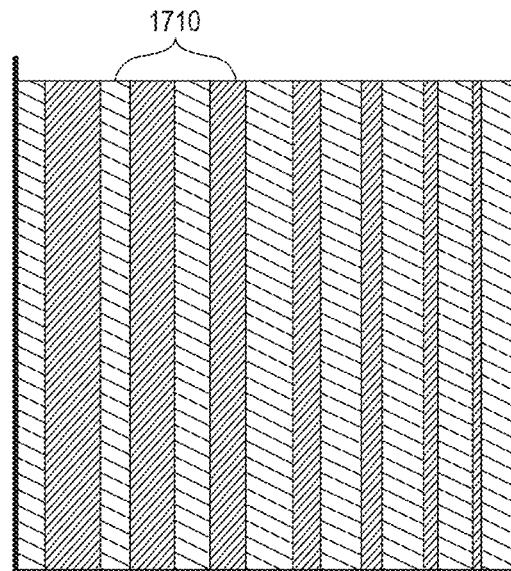
FIGS. 17A and 17B are diagrams illustrating a simplified model of a porous structure comprising an array of polymer channels having different sizes that is useful for estimating evaporation rate of the solvent from a porous structure.
Figure 17B:
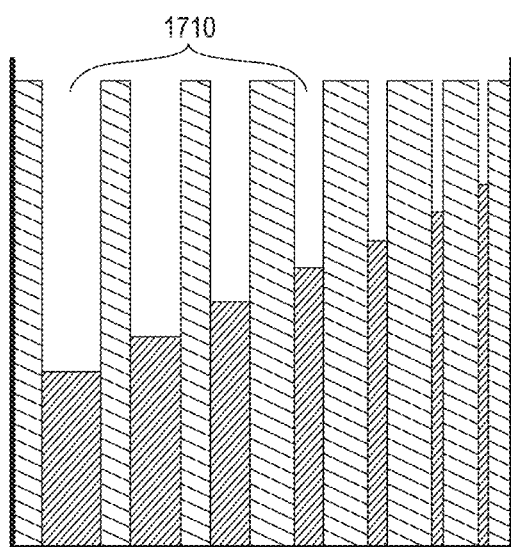
Figure 18:
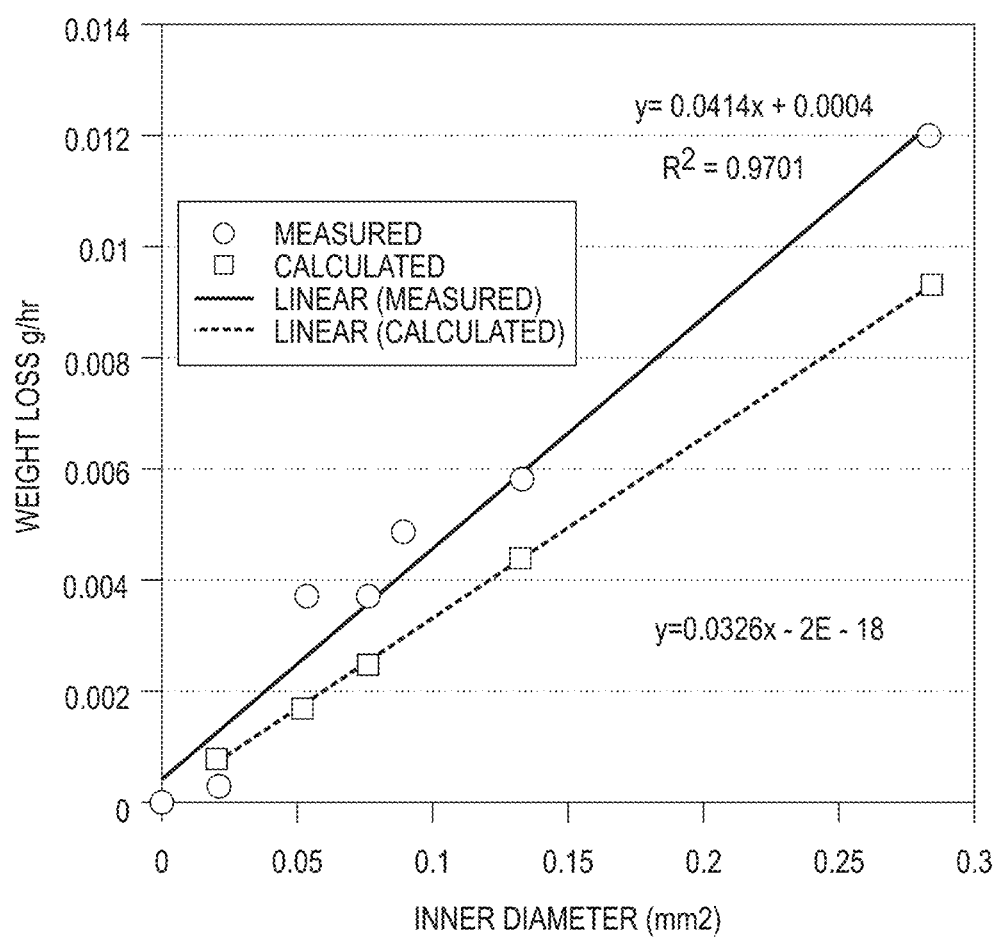
FIG. 18 shows graphs of the measured and calculated evaporation rates from the experiment based on the model of FIGS. 17A and 17B.

This evaporation model was further verified by an experiment in which the evaporation rate was simulated based on different size polymer channels 1710 filled with the solvent as illustrated in FIGS. 17A and 17B. The evaporation rate of solvent at the evaporation conditions can be calculated from the solvent lost during an amount of time in the different pore size channels. FIG. 17A shows the solvent in the channels 1710 at the beginning of the simulation and FIG. 17B shows the solvent in the channels at the end of the simulation. The experiment used different size needles with gauges on a syringe filled with the same amount of solvent to simulate the evaporation condition. By using a needle gauge to simulate the different pore size and fix the diffusion path length, the average weight loss of solvent in different pore sized channels can be calculated. The calculated evaporation rate is ~0.03 g/hr/mm2. By measure the weight different at the begin and the end of the experiment, the average weight loss of solvent in different syringe with different gauge sized needle can be measured and used to calculate the evaporation rate at this condition which his ~0.04 g/hr/mm2. The slight difference between the calculated and measure evaporation rate is probably from the leaking of the syringe and needle. FIG. 18 shows graphs of the measured and calculated evaporation rates from this experiment.

In some embodiments a biocompatible epoxy mixed with a sacrificial solvent can be used to fabricate a 3D scaffold. For example, 50 wt % of solvent may be used with mixing and printing procedure performed as describe above.

Figure 19:
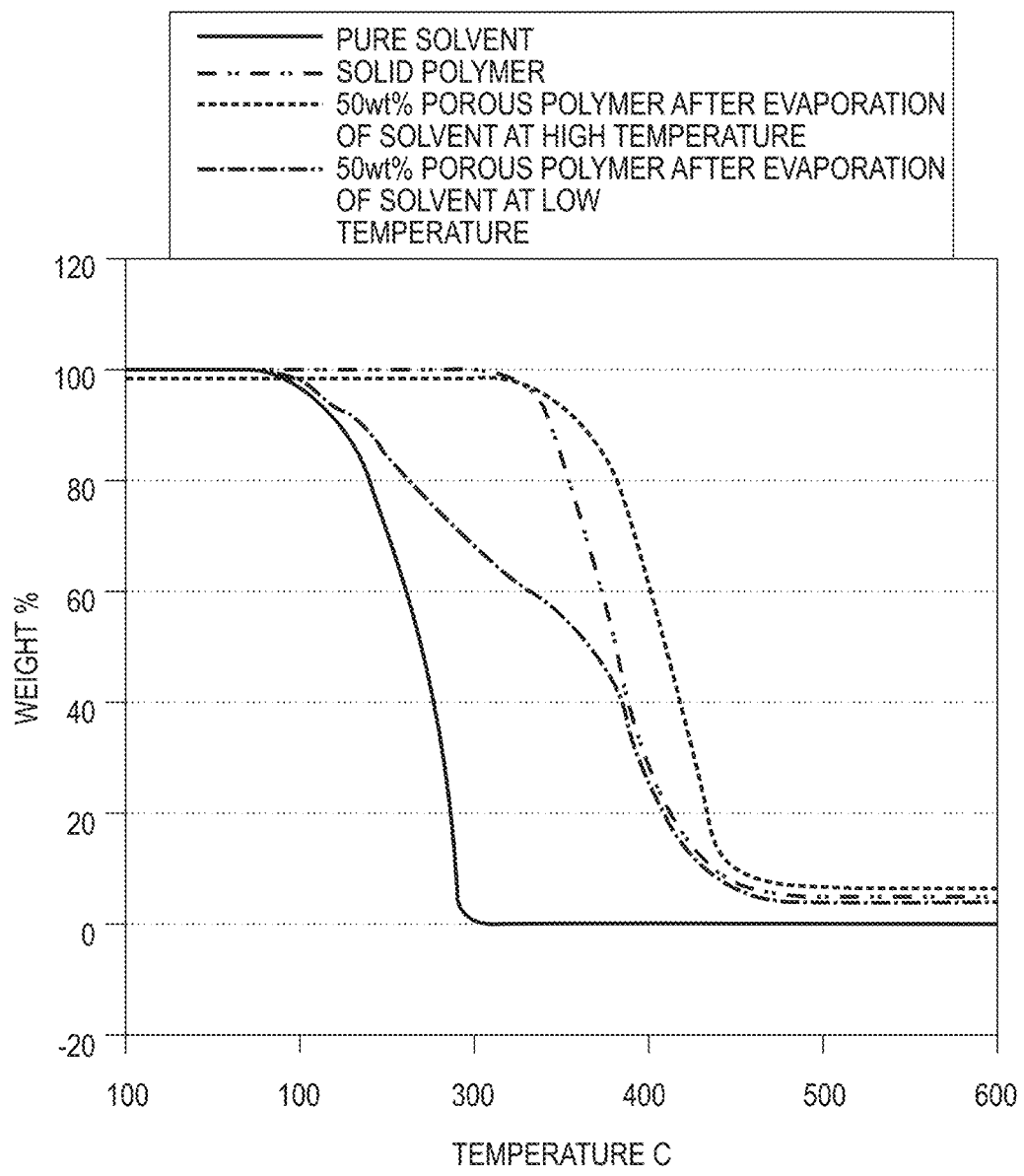
FIG. 19 shows the comparison of thermogravimetric analysis for a pure solvent, solid polymer, and 50 wt % solvent after evaporation for 10 hr at 120° C. and 220° C. under vacuum.

Thermogravimetric analysis performed to determine the total removal of the solvent after evaporation procedure for a structure prepared with 50 wt % of solvent using the printing procedure outlined above. FIG. 19 shows the comparison of weight % of the pure solvent, solid polymer, and printed 50 wt % biocompatible porous polymer after evaporation under vacuum.

The porosity of the printed and evaporated sample was calculated from its density according to equation [1] above. The theoretical porosities and densities of samples are calculated from the theoretical densities and wt % of each composites in the samples. The measured densities are calculated by dividing the weight (measured by balance) by the volume (measured by water displacement).

TABLE 3 summarizes the results of density of cured sample with 0% and 50 wt % of solvent. The ~50% of porosity indicates the porous structure of the 50 wt % sample.

TABLE 2

| wt % of solvent | 50 | 0 |
|---|---|---|
| Density g/cc | 0.58 | 1.16 |
| Porosity % | 49.6 | 0 |

Figure 20:
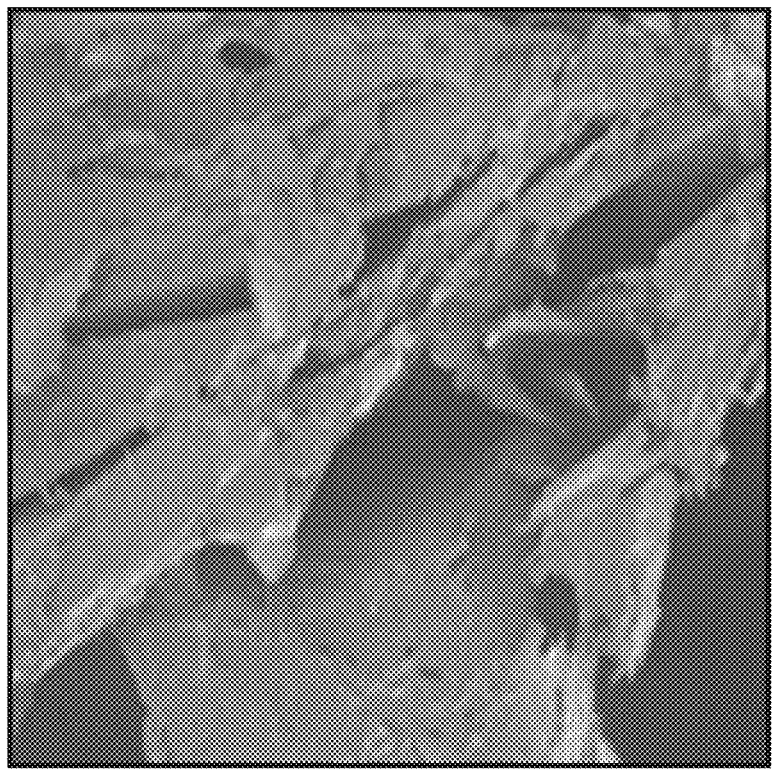
FIG. 20 is a SEM of a 50 wt % sample having pore sizes of ranging from 10 to 100 um.
Figure 21:
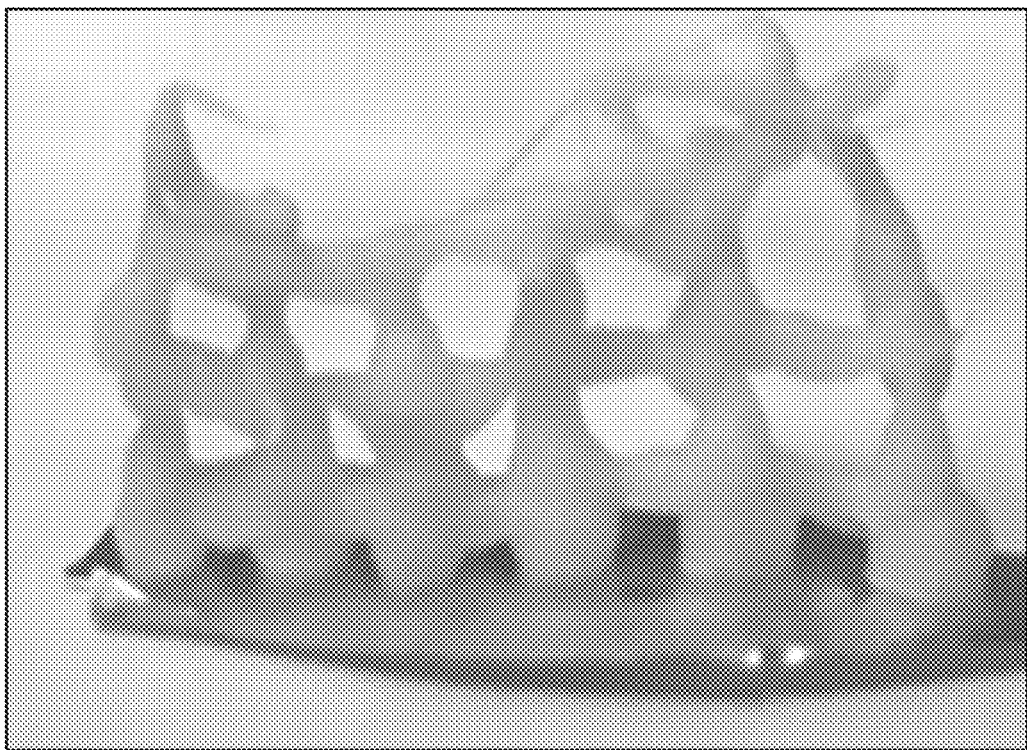
FIG. 21 is a photograph of a 3D printed 50 wt % cured and evaporated scaffold structure.

The porous structure was further investigated by the SEM image shown in FIG. 20. The pore size of the 50 wt % sample is around 10 to 100 µm. FIG. 21 is a photograph of the 3D printed 50 wt % cured and evaporated scaffold structure.

Figure 22:
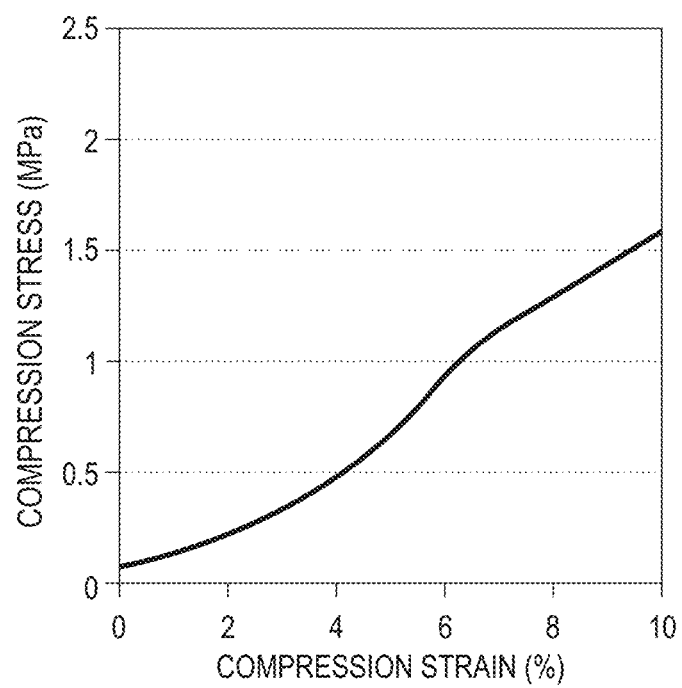
FIG. 22 presents the compressive curve at the elastic region for the 3D printed 50 wt % cured and evaporated scaffold structure of FIG. 21.

This example indicates the good printability of the formulation. To show the benefit of thermoset scaffold, the compressive test was implemented. FIGS. 22A and 22B presents the compressive curve at the elastic region (FIG. 22A) and the whole region (FIG. 22B). The compressive modulus and yield strength is calculated at the elastic region to be 24 MPa and 1.06 MPa which are higher than the other porous polymer for scaffold. Also, the ~2 MPa absorbed energy shows this porous material has good shock absorption properties.

To ensure that nutrient can transport within the porous polymer, the polymer's contact angle was tested. The contact angle of the solid epoxy is ~65° which shows its hydrophilic nature and ability to transport nutrient and promote cell attachment.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Various modifications and alterations of the embodiments discussed above will be apparent to those skilled in the art, and it should be understood that this disclosure is not limited to the illustrative embodiments set forth herein. The reader should assume that features of one disclosed embodiment can also be applied to all other disclosed embodiments unless otherwise indicated. It should also be understood that all U.S. patents, patent applications, patent application publications, and other patent and non-patent documents referred to herein are incorporated by reference, to the extent they do not contradict the foregoing disclosure.

The invention claimed is:

1. A method of forming a porous structure, comprising: mixing a solvent with a curable material comprising a thermoset monomer precursor which disperses in the solvent to form a mixture comprising greater than 50% solvent content; three-dimensionally printing the mixture on a substrate using a three-dimensional (3D) printer; increasing, after three-dimensionally printing, a viscosity of the mixture; curing the curable material on the substrate to allow polymerization of the curable material while a shape of the curable material is maintained by the solvent; and removing the solvent from the structure, the structure comprising pore diameters that are below a resolution of the 3D printer, wherein the pore diameters range from 10 to 100 µm.

2. The method of claim 1, wherein the mixture further comprises one or more of fillers, polymers, and nanoparticles.

3. The method of claim 1, wherein increasing the viscosity of the mixture comprises reducing a temperature of the mixture.

4. The method of claim 1, wherein increasing the viscosity of the mixture comprises chemically reacting the solvent.

5. The method of claim 1, wherein increasing the viscosity of the mixture comprises increasing the viscosity due to non-Newtonian behavior of the solvent.

6. The method of claim 1, wherein increasing the viscosity of the mixture comprises using shear controlling particles in the mixture.

7. The method of claim 1, wherein removing the solvent comprises vacuum removal of the solvent.

8. The method of claim 1, wherein removing the solvent comprises dissolving the solvent in a second solvent.

9. The method of claim 1, wherein removing the solvent comprises melting the solvent.

10. The method of claim 1, wherein curing the curable material and removing the solvent causes shrinkage less than about 20% of the structure.

11. The method of claim 1, wherein curing the curable material and removing the solvent produces the structure having porosity greater than 50%.

12. The method of claim 1, wherein the mixture includes a curing initiator for the curable material.

13. The method of claim 12, wherein the curing initiator for the curable material is introduced after increasing the viscosity of the solvent.

14. The method of claim 12, wherein the curing initiator is introduced by one or more of vapor deposition, vapor diffusion and liquid permeation.

15. The method of claim 1, wherein three dimensionally printing the mixture comprises ink jet printing the mixture.

16. The method of claim 1, wherein three dimensionally printing the mixture comprises extruding the mixture.

17. The method of claim 1, wherein curing the curable material comprises activating the curing by one or more of heat, light, pressure, and ultrasound.

18. The method of claim 1, wherein the curable material comprises one or more of epoxy resin, polyester resin, polyurethanes, vulcanizable rubber, polyimides, silicone, and vinyl ester.

19. The method of claim 1, wherein the curable material comprises the thermoset monomer precursor combined with a thermoplastic material.

20. The method of claim 19, wherein the curable material further comprises one or more of a polymer comprising lactide and glycolide, chitosan, hydroxybutyric acid, polyanhydrides, polyester, polyphosphazenes, polyphosphoester, caprolactone polymer, alginate, agar, polyurethane, and/or gelatin.

21. The method of claim 1, wherein the structure comprises pore diameters that are smaller than a nozzle size of the 3D printer.

22. The method of claim 1, wherein the structure comprises a biologically compatible three-dimensional porous scaffold structure.

23. The method of claim 1, wherein the structure has a porosity of >50% and a mechanical modulus of >20 MPa.

24. The method of claim 1, wherein the structure has a porosity of >50% and a compressive strength of about 1 MPa.

25. The method of claim 1, wherein the structure has a porosity of >50%, a mechanical modulus of >20 MPa, and a compressive strength of about 1 MPa.

* * * * *